United States Patent [19]
Bolinger et al.

[11] Patent Number: 6,127,582
[45] Date of Patent: *Oct. 3, 2000

[54] HYDROFORMYLATION PROCESS

[75] Inventors: Cornelius Mark Bolinger, Sugar Land, Tex.; Peter Arnoldy; Wilhelmus Petrus Mul, both of Amsterdam, Netherlands

[73] Assignee: Shell Oil Company, Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/918,981

[22] Filed: Aug. 27, 1997

[51] Int. Cl.$^7$ .................................................... C07C 45/50
[52] U.S. Cl. ........................................... 568/454; 568/451
[58] Field of Search ...................... 568/454, 451

[56] References Cited

U.S. PATENT DOCUMENTS 5,288,918  2/1994  Maher et al. ........................... 568/454

FOREIGN PATENT DOCUMENTS

0495547 A2  1/1992  European Pat. Off. ........ C07C 51/14
95/05354  2/1995  WIPO .

Primary Examiner—Sreeni Padmanabhan

[57] ABSTRACT

A process for the hydroformylation of ethylenically unsaturated compounds with carbon monoxide and hydrogen in the presence of a catalyst system comprising
a) a source of platinum group metal cations;
b) a source of non-halide anions;
c) a source of at least one bidentate ligand of the formula $$R^1R^2M^1RM^2R^3R^4 \qquad (I)$$

wherein $M^1$ and $M^2$ independently represent a phosphorus, arsenic or antimony atom, R represents a bivalent bridging group containing from 1–4 atoms in the bridge, $R^1$ and $R^2$ together represent a bivalent substituted or unsubstituted cyclic group whereby the two free valencies are linked to $M^1$, and $R^3$ and $R^4$ independently represent a substituted or unsubstituted hydrocarbyl group, or together represent a bivalent substituted or unsubstituted cyclic group whereby the two free valencies are linked to $M^2$; and
d) a source of halide anions chosen from the group of chloride, iodide and bromide and mixtures thereof, characterized by the additional presence of water, in an amount of more than 0.6 wt % based on the total of the reaction mixture and up to its solubility limit under the reaction conditions.

15 Claims, No Drawings

HYDROFORMYLATION PROCESS

FIELD OF THE INVENTION

The invention relates to a process for the hydroformylation of ethylenically unsaturated compounds by reaction thereof with carbon monoxide and hydrogen in the presence of a catalyst.

BACKGROUND OF THE INVENTION

The hydroformylation of ethylenically unsaturated compounds to form aldehydes and/or alcohols, is of considerable industrial importance. The process has been in commercial operation for decades and over the years much development work has been done to optimize the reaction conditions, the catalyst system and the equipment.

Although significant progress towards higher yield and product selectivity has been made, further improvement of the process is still needed.

In EP-B 0 495 547 there is disclosed a monocarbonylation process whereby the catalyst system comprises a source of palladium cations, a source of anions, and a bidentate diphosphine as defined below. In hydroformylating olefins, the activity and selectivity of this catalyst system is still not entirely satisfactory.

In WO 95/05354 there is disclosed a hydroformylation process whereby the catalyst system comprises a source of platinum group metal cations, a source of anions other than halide anions, a source of bidentate ligands as defined below and a catalyst promoter comprising a source of halide anions in a molar ratio halide anion: platinum group metal cation of at most 3:1. It is shown that the presence of the halide ion accounts for a considerably enhanced activity and selectivity of the process towards the desired alcohol products. However, this process appears to be exceedingly sensitive to small variations in halide ion concentration, the positive effect of which having a sharp peak at a molar ratio to the cation of about 0.4:1. In Examples 10–12 of WO 95/05354 tin chloride was the promoter used and water was added to an amount of 0.6 wt %, calculated on the total of the reaction mixture. However, any particular effect of the water was not recognised and cannot be deduced from this document.

SUMMARY OF THE INVENTION

It has now been found that water, when added in an amount of more than 0.6 wt % based on the total of the reaction mixture and up to its solubility limit in the reaction mixture under the reaction conditions and in particular up to 3 wt %, acts as a strong co-promoter with the halide anion.

Accordingly, the present invention relates to a process for the hydroformylation of ethylenically unsaturated compounds with carbon monoxide and hydrogen in the presence of a catalyst system comprising
a) a source of platinum group metal cations;
b) a source of non-halide anions;
c) a source of at least one bidentate ligand of the formula

$$R^1R^2M^1RM^2R^3R^4 \quad (I)$$

wherein $M^1$ and $M^2$ independently represent a phosphorus, arsenic or antimony atom, R represents a bivalent bridging group containing from 1–4 atoms in the bridge, $R^1$ and $R^2$ together represent a bivalent substituted or unsubstituted cyclic group whereby the two free valencies are linked to $M^1$, and $R^3$ and $R^4$ independently represent a substituted or unsubstituted hydrocarbyl group, or together represent a bivalent substituted or unsubstituted cyclic group whereby the two free valencies are linked to $M^2$; and
d) a source of halide anions chosen from the group of chloride, iodide and bromide and mixtures thereof, characterised in that the hydroformylation is conducted in the presence of water, in an amount of more than 0.6 wt % based on the total weight of the reaction mixture and up to its solubility limit under the reaction conditions.

Preferably, the molar ratio between the halide anions and the platinum group metal is between 0.02:1 and 3:1.

Preferably, the amount of water is between 0.7–3.0 wt %, based on the total weight of the reaction mixture.

DETAILED DESCRIPTION OF THE INVENTION

Previously, there existed a maximum limit on the ratio of halide anion/metal content when conducting hydroformylation in the presence of 0.6 wt % or less of water at which point the catalytic activity peaked, and further increases in the halide anion/metal ratio only decreased catalytic activity. Now, we have found that this otherwise maximum halide anion/metal ratio can be increased with observable increases in catalytic activity by rasing the amount of water in the reaction mixture to greater than 0.6 wt. %.

In another embodiment, the catalyst activity can also be increased without raising the otherwise maximum limit on the halide anion/metal molar ratio by simply raising amount of water beyond 0.6 wt. %.

The weight percent of water in the reaction mixture is based upon the weight of all ingredients present in the liquid phase in the hydroformylation reaction zone, including the ethylenically unsaturated compounds, dissolved hydrogen, dissolved carbon monoxide, water, and the catalyst system.

In the present specification the metals of the platinum group are defined as the metals with the atomic numbers 28, 46 and 78, i.e. nickel, palladium and platinum. Of these, palladium and platinum are preferred.

Examples of suitable metal sources are platinum or palladium compounds such as salts of palladium and nitric acid, sulphuric acid or sulphonic acids, salts of platinum or palladium and carboxylic acids with up to 12 carbon atoms, palladium- or platinum complexes, e.g. with carbon monoxide or acetylacetonate, or palladium combined with a solid material such as an ion exchanger or carbon. Palladium (II) acetate and platinum(II) acetylacetonate are examples of preferred metal sources.

As anion source, other than halide anions, any compound generating these anions may be used. Suitably, acids, or salts thereof, are used as source of anions, for example any of the acids mentioned above, which may also participate in the salts of the metals of the platinum group.

In the catalyst systems of the invention, preferably strong acids are used as anion source, i.e. acids having a pKa value of less than 3, preferably less than 2, measured in aqueous solution at 18° C. The anions derived from these acids are non-coordinating or weakly coordinating with the metals of the platinum group.

Typical examples of suitable anions are anions of phosphoric acid, sulphuric acid, sulphonic acids and halogenated carboxylic acids such as trifluoroacetic acid.

Sulphonic acids are in particular preferred, for example methanesulphonic acid, trifluoromethanesulphonic acid, tert-butanesulphonic acid, p-toluenesulphonic acid and 2,4, 6-trimethylbenzenesulphonic acid.

Complex anions are also suitable, such as the anions generated by a combination of a Lewis acid such as $BF_3$, AlCl$_3$, SnF$_2$, Sn(CF$_3$SO$_3$)$_2$, SnCl$_2$ or GeCl$_2$, with a protic acid, such as a sulphonic acid, e.g. CF$_3$SO$_3$H or CH$_3$SO$_3$H or a hydrohalogenic acid such as HF of HCl, or a combination of a Lewis acid with an alcohol. Examples of such complex anions are BF$_4$—, SnCl3—, [SnCl$_2$ . CF$_3$SO$_3$]— and PF$_6$—.

In bidentate ligands of formula (I), i.e., component c of the catalyst system, M$^1$ and M$^2$ are preferably the same and, more preferably, are both phosphorus atoms, in which case the ligands are bisphosphines.

In the bridging group, represented by R, typically all bridging groups are carbon atoms. Preferably the bridging group contains two or three, more preferably two, carbon atoms in the bridge. Thus, exemplary organic bridging groups R are CH$_2$—CH$_2$ and CH$_2$—CH$_2$—CH$_2$.

The bivalent (substituted) cyclic group, represented by R$^1$ together with R$^2$, in general comprises at least 5 ring atoms and preferably contains from 6 to 9 ring atoms. More preferably the cyclic group contains 8 ring atoms. Substituents, if any, are usually alkyl groups having from 1 to 4 carbon atoms. As a rule, all ring atoms are carbon atoms, but bivalent cyclic groups containing one or two heteroatoms in the ring, such as oxygen- or nitrogen, atoms are not precluded. Examples of suitable bivalent cyclic groups are 1,4-cyclohexylene, 1,4-cycloheptylene, 1,3-cycloheptylene, 1,2-cyclooctylene, 1,3-cyclooctylene, 1,4-cyclooctylene, 1,5-cyclooctylene, 2-methyl-1,5-cyclooctylene, 2,6-dimethyl-1,4-cyclooctylene and 2,6-dimethyl-1,5-cyclooctylene groups.

Preferred bivalent cyclic groups are selected from 1,4-cyclooctylene, 1,5-cyclooctylene, and methyl (di)substituted derivatives thereof.

Mixtures of ligands comprising different bivalent cyclic groups may be used as well, e.g. mixtures of ligands with 1,4-cyclooctylene and ligands with 1,5-cyclooctylene groups.

In the ligands of formula (I), R$^3$ and R$^4$ may independently represent various non-cyclic or cyclic groups, optionally substituted with substituents such as alkoxy groups with 1 to 4 carbon atoms, halogen atoms or (C$_1$ to C$_4$ alkyl)amino groups.

Examples are alkyl groups such as ethyl, isopropyl, sec-butyl and tert-butyl groups, cycloalkyl groups such as cyclopentyl and cyclohexyl groups, aryl groups such as phenyl and tolyl groups and bivalent groups such as a hexamethylene group. However, preferably R$^3$, together with R$^4$ represents a bivalent cyclic group, in particular the same group as the group represented by R$^1$ together with R$^2$, in which case the two free valencies of the bivalent cyclic group are, of course, linked to M$^2$, instead of M$^1$. Thus, preferred bidentate ligands of formula (I) are 1,2-bis(1,4-cyclooctylenephosphino)ethane, 1,2-bis(1,5-cyclooctylenephosphino)ethane and mixtures thereof.

For the preparation of the bidentate ligands, reference is made to known techniques, for example the method disclosed in GB-A-1,127,965.

The quantity in which the catalyst system is used, is not critical and may vary within wide limits. Usually amounts in the range of 10$^{-8}$ to 10$^{-1}$, preferably in the range of 10$^{-7}$ to 10$^{-2}$ mole atom of platinum group metal per mole of ethylenically unsaturated compound are used. The amounts of the participants in the catalyst system are conveniently selected such that per mole atom of platinum group metal from 0.5 to 10, preferably from 1 to 6 moles of bidentate ligand are used, from 0.5 to 15, preferably from 1 to 8 moles of anion source or a complex anion source.

The molar ratio between halide anions and platinum group metal cations is preferably not more than 3:1. If larger amounts of halide anions are present, the activity of the catalyst system tends to be adversely affected, presumably because of coordination occurring between palladium and halide moieties.

Preferably, the molar ratio between halide anions and platinum group metal cations is at most 2:1, more preferably less than 1:1, for instance from 0.02:1 to 1:1. In an embodiment of the invention, the molar ratio of halide anions to metal, such as chloride to platinum or palladium, is from 0.4:1 to 1:1. Since previous attempts at raising the molar ratio limit beyond about 0.3–0.4:1 failed to increase the activity of the catalyst when 0.6 wt. % water was used, in this embodiment higher ratios of anion to metal with resulting increases in catalyst activity are employed.

As source of halide anions any compound generating halide anions under the reaction conditions may be used.

Recommended are inorganic compounds such as hydrogen halides, e.g. HCl, HBr and HI and metal halides, e.g. NaCl, MgBr$_2$, ZnCl$_2$, ZnI$_2$, KBr, RbCl, CsCl, CsI, MgI$_2$ and CuCl.

Another category of recommended sources of halide anions consists of halogen containing organic compounds which are capable of providing halide anions to the reaction medium. Suitable are for example organic phosphonium halides, such as triarylalkyl phosphonium chloride and halogen containing aromatic compounds such as 5-halobenzoic acids, e.g. 5-chlorobenzoic acid, 2,5-dichlorobenzoic acid, 2,3,5-triiodobenzoic acid, 3,5-di-iodobenzoic acid, m-halophthalic acids and esters thereof.

Catalyst promoters comprising a source of chloride anions are in particular preferred.

The ethylenically unsaturated compound, used as starting material, is preferably an olefin having from 2 to 30 carbon atoms per molecule, or a mixture thereof. They may comprise one or more double bonds per molecule. Preferred are internal olefins having from 4 to 24 carbon atoms, or mixtures thereof. Such olefin mixtures are commercially readily available, for example as products of a process for the oligomerization of ethylene, followed by a double bond isomerization and disproportionation reaction. In the process of the invention, these internal olefins, usually mixtures of linear internal olefins with 6 to 20 carbon atoms per molecule, or closer boiling fractions of such mixtures, can be hydroformylated at high rates and an almost complete conversion. Examples are mixtures of linear internal C$_6$ to C$_8$ olefins, and of linear internal C$_{10}$ to C$_{14}$ olefins.

Substituted olefins may also be used, for example unsaturated carboxylic acids, esters of such acids, or unsaturated esters of carboxylic acids, e.g. allylacetate.

If desired, branched olefins such as propene trimer or isomeric butene dimers ("DIMERSOL" a trademark) may be used, but the hydroformylation product will then, of course, contain branched structures as well.

Also, olefinically unsaturated polymeric feedstock, such as atactic polyolefins like 'Shube's' (mixture of oligomers of C$_{16}$-olefins), "NAPVIS" and "HYVIS" (trademarks for low molecular weight polyisobutylene) and styrene-butadiene (block)copolymers may be converted into interesting alcohols (as intermediates to synthetic lubricants, functionalized additives, etc.).

Finally, alpha-olefins, such as 1-octene and propene, and diolefins, such as norbornadiene, dicyclopentadiene, 1,5-hexadiene and 1,7-octadiene may be used. The diolefins will of course yield (predominantly) a di-hydroformylated product, although also mono-hydroformylated may be formed.

Hydrogen and carbon monoxide may be supplied in equimolar or non-equimolar ratios, e.g. in a ratio within the range of 8:1 to 1:4, typically 4:1 to 1:2. Preferably they are supplied in a ratio within the range of 3:1 to 1:2.

The hydroformylation can be suitably carried out at moderate reaction conditions. Hence temperatures in the range of 50 to 200° C. are recommended, preferred temperatures being in the range of 70 to 160° C. Reaction pressures in the range of 5 to 100 bar are preferred, lower or higher pressures may be selected, but are not considered particularly advantageous. Moreover, higher pressures require special equipment provisions.

In the process of the invention, the ethylenically unsaturated starting material and the formed hydroformylation product may act as reaction diluent. Hence, the use of a separate solvent is not necessary. Conveniently, however, the hydroformylation reaction may be carried out in the additional presence of a solvent. As such, saturated hydrocarbons, e.g. paraffins and isoalkanes are recommended and furthermore alcohols, preferably having from 4 to 10 carbon atoms per molecule, such as butanol, ethylhexanol-1, nonanol-1, or in general terms the alcohols formed as hydroformylation product; ethers such as 2,5,8-trioxanonane (diglyme), diethylether and anisole, and ketones, such as methylbutylketone.

In earlier hydroformylation processes, such as the process according to EP-A-0,495,547, the use of an alcohol as solvent was often considered undesirable, since the used hydroformylation catalysts were also catalytically active in the formation of esters in a reaction involving an olefin, carbon monoxide and the solvent alcohol. However, the catalyst systems of the present invention in view of their high selectivity towards the desired hydroformylation product, allow the use of alcohols as solvent.

Solvents containing strong polar groups are in particular preferred if the unsaturated starting material has a relatively low molecular weight, i.e., if ethylenically unsaturated compounds having from 5 to 7 carbon atoms are used.

For the hydroformylation of higher molecular weight unsaturated compounds, e.g. olefins having from 10 to 18 carbon atoms the use of less polar inert solvents will usually be satisfactory.

Solvents, comprising or substantially consisting of sulphones are preferred. Sulphones are in particular preferred, for example dialkylsulphones such as dimethylsulphone and diethylsulphone and cyclic sulphones, such as sulfolane (tetrahydrothiophene-2,2-dioxide), sulfolene, 2-methylsulfolane and 2-methyl-4-ethylsulfolane.

Sulfolane has proved to be a most effective solvent for the formation of a multiphase liquid reaction medium.

Mixtures of solvents may also be used, for example a mixture of a sulphone with a protic solvent, such as an alcohol. In the hydroformylation of olefins, typically an alcohol is selected which is identical or similar to an alcohol as obtained in the hydroformylation reaction.

The amount of solvent to be used in the process of the invention may vary considerably. It is within the reach of those skilled in the art to establish in each case the degree of cooling and the optimal amount of solvent required for the formation of a multiphase liquid reaction medium. The experimental results provided hereinafter, are also indicative for the amount of solvent, preferably to be used.

The process of the invention is eminently suitable to be used for the preparation of alcohols from internal olefins at high rate, in particular by using a catalyst system as defined above, based on palladium as the platinum group metal.

Furthermore the process is very useful for the preparation of aldehydes having a high linearity, in particular by using a catalyst system as defined above, based on platinum as platinum group metal.

The invention will be illustrated by the following examples. The abbreviations have the following meanings:

BCPE=1,2-bis(1,4-cyclooctylenephosphino)ethane
TFSA=trifluoromethanesulphonic acid
EH=2-ethylhexan-1-ol

EXAMPLES

In the Examples, the hydroformylation of an $C_{11}/C_{12}$ olefin mixture, isomerised to equilibrium (i.e. mainly internal linear olefins), with carbon monoxide and hydrogen in the presence of a Pd/BCPE/TFSA catalyst composition and varying amounts of chloride and water was followed by analysing samples by Gas Chromatography (GC).

At the end of the reaction (the duration of which depends on the activity of the catalytic system) the selectivity to the $C_{12}/C_{13}$ alcohol end-product was >98 mol %, the linearity of the alcohols produced was 75 mol % and the amounts of paraffins produced less than 1 mol % in all cases.

The differences between the results are in the activity, as expressed by the first-order reaction rate constant k. Assuming that the conversion of olefin to alcohol is of first order in both the olefin and the metal (Pd), k is expressed per hour per mol Pd and calculated for batch operation according to the formula $$k = (1/[Pd]) \cdot 1 \, \ln\{(100-X)/t\}$$

wherein [Pd] is the mol amount of Pd used, X the mol % of olefin converted and t the time in hours.

Example 1

(NaCl/Pd=0.1, H$_2$O=0.6 wt %)

An experiment was carried out in a 300 ml stirred batch autoclave. The autoclave was charged with 77.68 ml $C_{11}/C_{12}$ isomerised olefin, 64.47 ml EH, and 0.81 ml water. After being flushed the autoclave was pressurised with hydrogen and carbon monoxide in a molar ratio of 2:1 to a pressure of 5000 kPa and heated to 105° C. The catalyst solution (0.475 mmol palladium(II)acetate, 0.665 mmol BCPE, 0.0475 mmol NaCl, and 1.09 mmol TFSA dissolved in 16.4 ml sulfolane) was added to the content of the autoclave.
Reaction rate constant k=950

Example 2

(NaCl/Pd=0.3: H$_2$O=0.6 wt %)

An experiment was carried out substantially as in Example 1, with the difference that 0.143 mmol NaCl was used.
Reaction rate constant k=2200

Example 3

(NaCl/Pd=0.8; H$_2$O=0.6 wt %)

An experiment was carried out substantially as in Example 1, with the difference that 0.38 mmol NaCl was used.
Reaction rate constant k=650

Example 4
(NaCl/Pd=0.3; H$_2$O=1.6 wt %)

An experiment was carried out substantially as in Example 1, with the difference that 2.16 ml water was applied and that the catalyst solution consisted of 0.25 mmol palladium(II)acetate, 0.3 mmol BCPE, 0.075 mmol NaCl, and 0.575 mmol TFSA dissolved in 16.4 ml sulfolane.
Reaction rate constant k=2200

Example 5
(NaCl/Pd=0.43: H$_2$O=1.6 wt %)

An experiment was carried out substantially as in Example 4, with the difference that 0.108 mmol NaCl was used.
Reaction rate constant k=3200

Example 6
(NaCl/Pd=0.7; H$_2$O=1.6 wt %)

An experiment was carried out substantially as in Example 4, with the difference that 0.175 mmol NaCl was used.
Reaction rate constant k=2600

Example 7
(NaCl/Pd=0.3; H$_2$O=2.4 wt %)

An experiment was carried out substantially as in Example 1, with the difference that 0.143 mmol NaCl and 3.24 ml water was used.
Reaction rate constant k=3500

Example 8
(NaCl/Pd=0.55; H$_2$O=2.4 wt %)

An experiment was carried out substantially as in Example 1, with the difference mmol NaCl and 3.24 ml water was used.
Reaction rate constant k=4100

Example 9
(NaCl/Pd=0.8; H$_2$O=2.4 wt %)

An experiment was carried out substantially as in Example 1, with the difference mmol NaCl and 3.24 ml water was used.
Reaction rate constant k=3300

These Examples and their results are summarised in the following Table.

TABLE

| Example No. | NaCl/Pd | H$_2$O, wt % | Reaction rate constant k |
| --- | --- | --- | --- |
| 1 | 0.1 | 0.6 | 950 |
| 2 | 0.3 | 0.6 | 2200 |
| 3 | 0.8 | 0.6 | 650 |
| 4 | 0.3 | 1.6 | 2200 |
| 5 | 0.43 | 1.6 | 3200 |
| 6 | 0.7 | 1.6 | 2600 |
| 7 | 0.3 | 2.4 | 3500 |
| 8 | 0.55 | 2.4 | 4100 |
| 9 | 0.8 | 2.4 | 3300 |

From these results it may be concluded, that the addition of water above 0.6 wt % enhances the activity-promoting effect of the halide. The halide/metal molar ratio at which maximum activity is observed is raised as well.

What we claim is:

1. A process for the hydroformylation of ethylenically unsaturated compounds with carbon monoxide and hydrogen in the presence of a catalyst system comprising
   a) a source of platinum group metal cations;
   b) a source of non-halide anions;
   c) a source of at least one bidentate ligand of the formula $$R^1R^2M^1RM^2R^3R^4 \qquad (I)$$

wherein $M^1$ and $M^2$ independently represent a phosphorus, arsenic or antimony atom, R represents a bivalent bridging group containing from 1–4 carbon atoms in the bridge, $R^1$ and $R^2$ together represent a bivalent substituted or unsubstituted cyclic group whereby the two free valencies are linked to $M^1$, and $R^3$ and $R^4$ independently represent a substituted or unsubstituted hydrocarbyl group, or together represent a bivalent substituted or unsubstituted cyclic group whereby the two free valencies are linked to $M^2$; and
   d) a source of halide anions chosen from the group of chloride, iodide and bromide and mixtures thereof;
said hydroformylation conducted in the presence of water in an amount of more than 0.6 wt % based on the total weight of the reaction mixture and up to its solubility limit under hydroformylation reaction conditions.

2. A process according to claim 1, characterized in that the molar ratio between the halide anions and the platinum group metal cations is between 0.02:1 and 3:1.

3. A process according to claim 2, characterized in that a) is a source of palladium or platinum cations.

4. A process according to claim 3, characterized in that b) is a strong acid having a pKa below 3.

5. A process according tq claim 4, characterized in that in the bidentate ligand of the formula (I) both of $M^1M^2$ phosphorus and R is or —CH$_2$—C$_2$—or —CH$_2$—CH$_2$—CH$_2$—.

6. A process according to claim 5, characterized in that in the bidentate ligand of formula (I) each of the bivalent cyclic groups, represented by $R^1$ together with $R^2$ and $R^3$ together with $R^4$ respectively, is a cycloalkylene group having from 6 to 9 ring atoms.

7. A process according to claim 6, characterized in that the halide anion comprises a chloride anion.

8. A process according to claim 7, characterized in that the amount of water is between 0.7–3.0 wt %, based on the total weight of the reaction mixture.

9. A process according to claim 1, characterized in that a) is a source of palladium or platinum cations.

10. A process according to claim 1, characterized in that b) is a strong acid having a pKa below 3.

11. A process according to claim 1, characterized in that the bidentate ligand of formula (I) both of $M^1$ and $M^2$ are phosphorus and R is CH$_2$—CH$_2$ or CH$_2$—CH$_2$—CH$_2$.

12. A process according to claim 1, characterized in that in the bidentate ligand of formula (I) each of the bivalent cyclic groups, represented by $R^1$ together with $R^2$ and $R^3$ together with $R^4$ respectively, is a cycloalkylene group having from 6 to 9 ring atoms.

13. A process according to claim 1, characterized in that the halide anion comprises a chloride anion.

14. A process according to claim 1, characterized in that the amount of water is between 0.7–3.0 wt %, based on the total weight of the reaction mixture.

15. A process according to claim 1, wherein a) comprises a source of palladium metal cations, and d) comprises a source of chloride anions.

* * * * *